United States Patent
Shin et al.

(10) Patent No.: US 8,317,708 B2
(45) Date of Patent: Nov. 27, 2012

(54) SETTING AN OPTIMAL IMAGE PARAMETER IN AN ULTRASOUND SYSTEM

(75) Inventors: Dong Kuk Shin, Seoul (KR); Sang Shik Park, Seoul (KR)

(73) Assignee: Medison Co., Ltd., Kangwon-do (KR)

( * ) Notice: Subject to any disclaimer, the term of this patent is extended or adjusted under 35 U.S.C. 154(b) by 300 days.

(21) Appl. No.: 12/848,014

(22) Filed: Jul. 30, 2010

(65) Prior Publication Data

US 2011/0054318 A1     Mar. 3, 2011

(30) Foreign Application Priority Data

Aug. 25, 2009   (KR) ........................ 10-2009-0078574

(51) Int. Cl.
*A61B 8/00*     (2006.01)
(52) U.S. Cl. ........................................ 600/443; 600/437
(58) Field of Classification Search .................. 600/437, 600/443, 450, 453
See application file for complete search history.

(56) References Cited

U.S. PATENT DOCUMENTS

| | | |
|---|---|---|
| 6,322,509 B1 | 11/2001 | Pan et al. |
| 2004/0267124 A1 | 12/2004 | Roundhill |
| 2005/0033175 A1 | 2/2005 | Lee et al. |
| 2008/0119735 A1 | 5/2008 | Lin et al. |

FOREIGN PATENT DOCUMENTS

| | | |
|---|---|---|
| KR | 10-2008-0085424 | 9/2008 |
| WO | WO 01/62155 A1 | 8/2001 |

OTHER PUBLICATIONS

Korean Office Action issued in Korean Patent Application No. 10-2009-0078574, dated Oct. 31, 2011.
European Search Report issued in European Patent Application No. EP 10170228.0 dated Dec. 8, 2010.

*Primary Examiner* — Michael Rozanski
(74) *Attorney, Agent, or Firm* — McDermott Will & Emery LLP

(57) ABSTRACT

A processing unit is configured perform an image process upon an ultrasound image to thereby detect a center of a blood vessel from the ultrasound image. The processing unit is configured to set the center of the blood vessel as an optimal focal point position. The processing unit is configured to calculate a plurality of steering angles, a plurality of transmit (Tx) frequencies and a plurality of sound speeds. The processing unit is further configured to form a plurality of ultrasound images corresponding to each of the steering angles, the Tx frequencies and the sound speeds based on the ultrasound data, detect a signal to noise ratio (SNR), a number of edge points of the blood vessel and a contrast difference between pixels for each of the second ultrasound images to thereby detect an optimal steering angle, an optimal Tx frequency and an optimal sound speed.

26 Claims, 11 Drawing Sheets

SETTING AN OPTIMAL IMAGE PARAMETER IN AN ULTRASOUND SYSTEM

CROSS-REFERENCE TO RELATED APPLICATIONS

The present application claims priority from Korean Patent Application No. 10-2009-0078574, filed on Aug. 25, 2009, the entire subject matter of which is incorporated herein by reference.

TECHNICAL FIELD

The present disclosure generally relates to ultrasound systems, and more particularly to setting an optimal image parameter for obtaining an optimal ultrasound image in an ultrasound system.

BACKGROUND

An ultrasound system has become an important and popular diagnostic tool since it has a wide range of applications. Specifically, due to its non-invasive and non-destructive nature, the ultrasound system has been extensively used in the medical profession. Modern high-performance ultrasound systems and techniques are commonly used to produce two or three-dimensional diagnostic images of internal features of a target object (e.g., human organs).

The ultrasound system can transmit and receive ultrasound signals to and from a target object to thereby form 2D (two-dimensional) or 3D (three-dimensional) ultrasound images of the target object.

The ultrasound system can form an optimal 2D or 3D ultrasound image based on an optimal image parameter. The optimal image parameter may include a focal point position, a steering angle, a transmit (Tx) frequency, a sound speed and the like. However, in the conventional ultrasound system, the optimal image parameter is set manually, not automatically. That is, a complicated manual set is required to optimize the 2D or 3D ultrasound image. Thus, diagnostic time becomes significantly longer.

SUMMARY

Embodiments for adaptively setting an optimal image parameter in an ultrasound system are disclosed herein. In one embodiment, by way of non-limiting example, an ultrasound system comprises: an ultrasound data acquisition unit configured to transmit and receive ultrasound signals to and from a target object including a blood vessel to thereby output ultrasound data; and a processing unit in communication with the ultrasound data acquisition unit and being configured to form an ultrasound image based on the ultrasound data, perform an image process upon the ultrasound image to thereby detect a center of the blood vessel from the ultrasound image, set the center of the blood vessel as an optimal focal point position, and calculate a plurality of steering angles, a plurality of transmit (Tx) frequencies and a plurality of sound speeds, wherein the ultrasound data acquisition unit is further configured to transmit and receive ultrasound signals to and from the target object in consideration of each of the steering angles, the Tx frequencies and the sound speeds to thereby output a plurality of ultrasound data, wherein the processing unit is further configured to form a plurality of ultrasound images corresponding to each of the steering angles, the Tx frequencies and the sound speeds based on the ultrasound data, detect a signal to noise ratio (SNR), a number of edge points of the blood vessel and a contrast difference between pixels for each of the second ultrasound images to thereby set an optimal steering angle, an optimal Tx frequency and an optimal sound speed based on the SNR, the number of edge points and the contrast difference.

In another embodiment, there is provided a method of setting an optimal image parameter, comprising: a) forming a first ultrasound image based on ultrasound data for a target object including a blood vessel; b) performing an image process upon the first ultrasound image to thereby detect a center of the blood vessel from the first ultrasound image; c) setting the center of the blood vessel as an optimal focal point position; d) forming a plurality of second ultrasound images corresponding to a plurality of steering angles for steering scanlines, wherein the steering angles are calculated by increasing/decreasing a maximum steering angle by predetermined angles; e) detecting a signal to noise ratio (SNR), a number of edge points of the blood vessel and a contrast difference between pixels for each of the second ultrasound images to thereby set an optimal steering angle based on the SNR, the number of edge points and the contrast difference; f) forming a plurality of third ultrasound images corresponding to a plurality of transmit (Tx) frequencies, wherein the Tx frequencies are calculated by increasing/decreasing a Tx frequency corresponding to the optimal steering angel by predetermined frequencies; g) detecting the SNR, the number of edge points and the contrast difference for each of the third ultrasound images to thereby set an optimal Tx frequency based on the SNR, the number of edge points and the contrast difference; h) forming a plurality of fourth ultrasound images corresponding to a plurality of sound speeds, wherein the sound speeds are calculated by increasing/decreasing a reference sound speed by predetermined values; and i) detecting the SNR, the number of edge points and the contrast difference for each of the fourth ultrasound images to thereby set an optimal sound speed based on the SNR, the number of edge points and the contrast difference.

In yet another embodiment, there is provided a method of setting an optimal image parameter, comprising: a) acquiring ultrasound data of a target object including a blood vessel; b) forming an ultrasound image based on the ultrasound data; c) performing an image process upon the ultrasound image to thereby detect a center of the blood vessel from the first ultrasound image; d) setting the center of the blood vessel as an optimal focal point position; e) calculating a plurality of steering angles, a plurality of transmit (Tx) frequencies and a plurality of sound speeds; f) acquiring a plurality of ultrasound data of the target object in consideration of each of the steering angles, the Tx frequencies and the sound speeds; g) forming a plurality of ultrasound images corresponding to each of the steering angles, the Tx frequencies and the sound speeds based on the ultrasound data; h) detecting a signal to noise ratio (SNR), a number of edge points of the blood vessel and a contrast difference between pixels for each of the second ultrasound images to thereby set an optimal steering angle, an optimal Tx frequency and an optimal sound speed based on the SNR, the number of edge points and the contrast difference.

The Summary is provided to introduce a selection of concepts in a simplified form that are further described below in the Detailed Description. This Summary is not intended to identify key or essential features of the claimed subject matter, nor is it intended to be used in determining the scope of the claimed subject matter.

DETAILED DESCRIPTION

A detailed description may be provided with reference to the accompanying drawings. One of ordinary skill in the art may realize that the following description is illustrative only and is not in any way limiting. Other embodiments of the present invention may readily suggest themselves to such skilled persons having the benefit of this disclosure.

Figure 1:
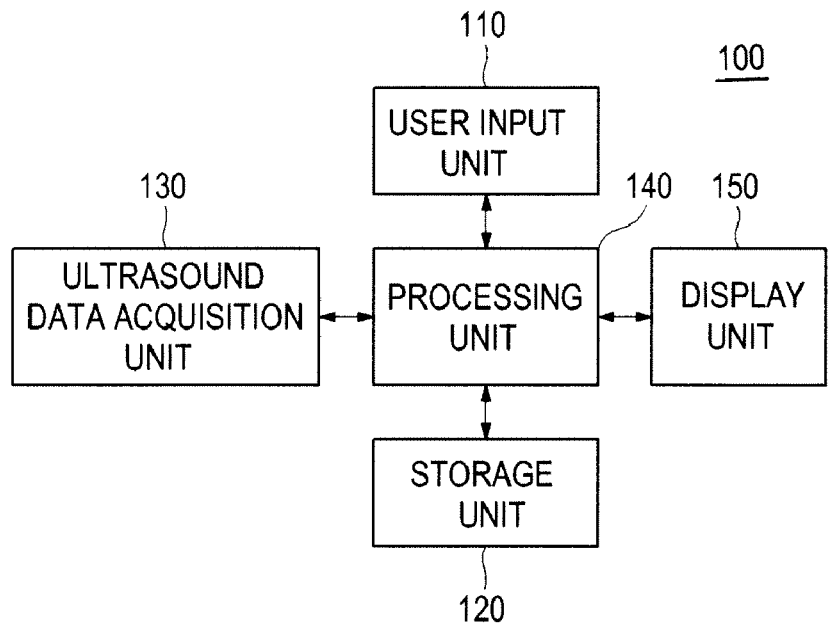
FIG. 1 is a block diagram showing an illustrative embodiment of an ultrasound system.

FIG. 1 is a block diagram showing an illustrative embodiment of an ultrasound system. Referring to FIG. 1, the ultrasound system 100 may include a user input unit 110. The user input unit 110 may be configured to receive input information from a user. In one embodiment, the input information may include first input information for setting a region of interest (ROI) on an ultrasound image or second input information for setting a seed point on the ultrasound image. The ultrasound image may be a brightness mode (B mode) image. However, it should be noted herein that the ultrasound image may not be limited thereto. The user input unit 110 may include a control panel, a mouse, a keyboard and the like.

The ultrasound system 100 may further include a storage unit 120. The storage unit 120 may store a blood vessel template corresponding to an object of interest (e.g., blood vessel) within a target object. Generally, the ultrasound system 100 may form an ultrasound image including the blood vessel based on a specific application, for example, a carotid application for observing the blood vessel. The blood vessel has a different size at every target object but has, morphologically, a unique and similar shape. Thus, the blood vessel template may be used to detect the blood vessel in the ultrasound image.

The storage unit 120 may further store a mapping table including transmit (Tx) frequencies and scan conditions. In one embodiment, the scan conditions may include depths (hereinafter, image depths) from a surface of the target object to a center of the blood vessel and steering angles for steering a plurality of scan-lines. However, it should be noted herein that the scan conditions may not be limited thereto.

Figure 2:
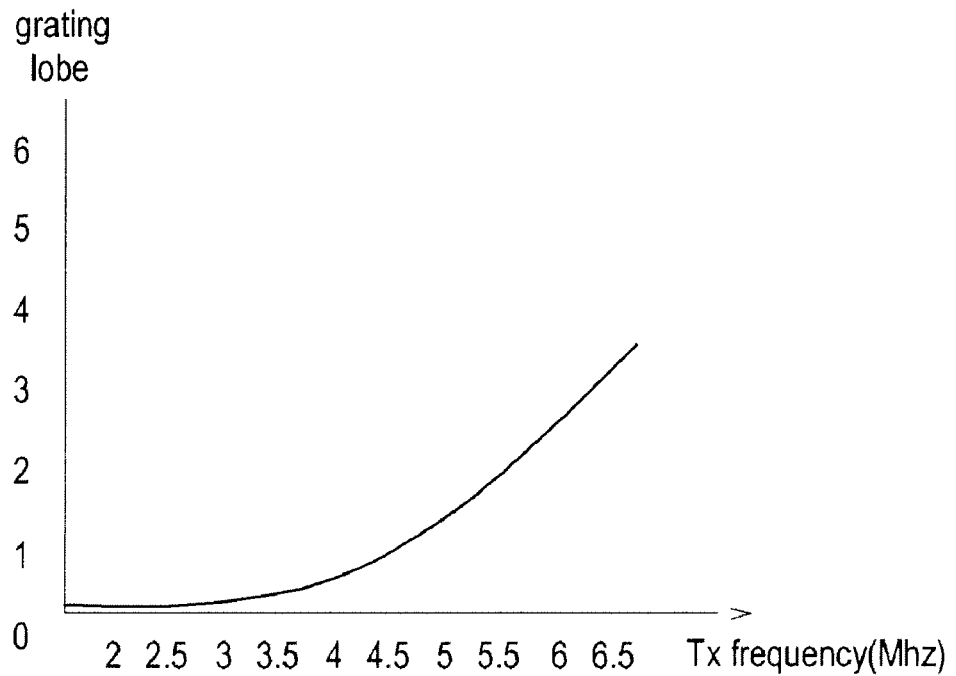
FIG. 2 is a graph showing an example of a grating lobe according to transmit (Tx) frequencies.

FIG. 2 is a graph showing an example of a grating lobe according to the transmit (Tx) frequencies. Generally, a grating lobe may mean unwanted emission of ultrasound from electronic array transducers. The grating lobe may be stronger as the Tx frequency becomes higher, as shown in FIG. 2. Further, the grating lobe may be stronger as the steering angle becomes larger (not shown).

Figure 3:
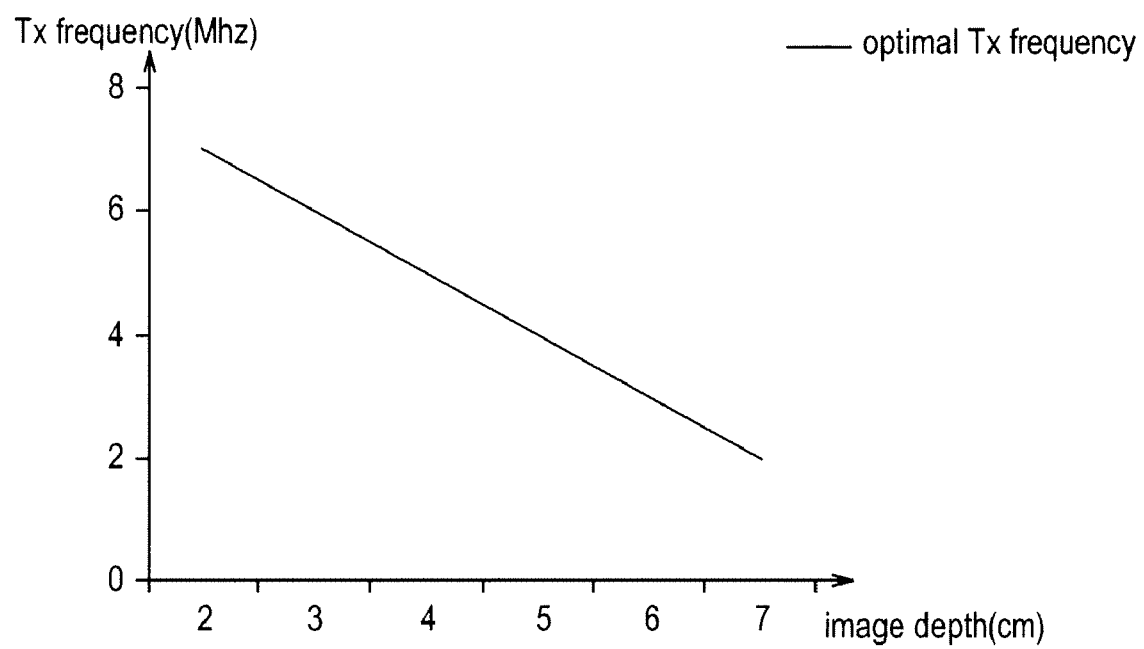
FIG. 3 is a graph showing an example of optimal Tx frequencies set according to image depths.

FIG. 3 is a graph showing an example of optimal Tx frequencies according to image depths. As shown in FIG. 3, a higher Tx frequency may be set as the optimal Tx frequency when an image depth is smaller. Also, a lower Tx frequency may be set as the optimal frequency when the image depth is larger.

Figure 4:
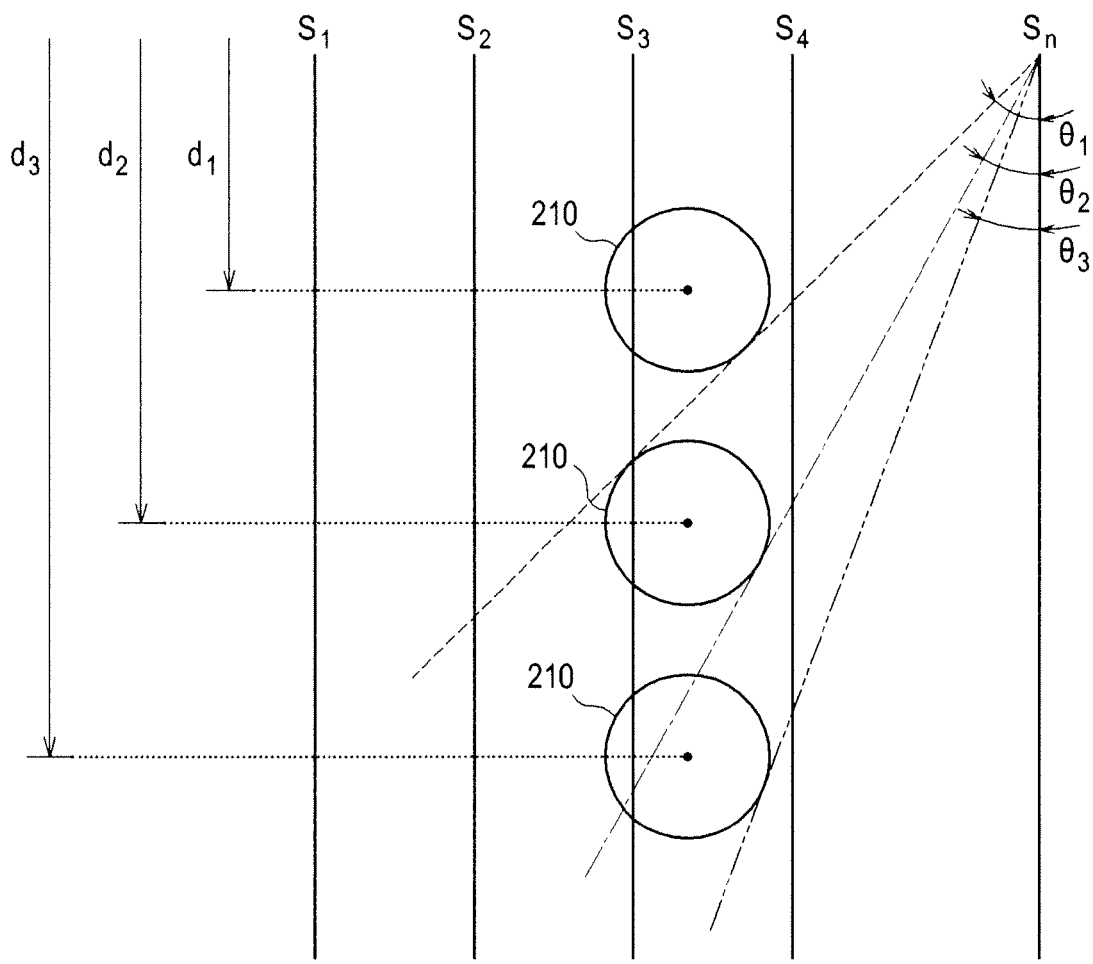
FIG. 4 is a schematic diagram showing an example of steering angles set according to the image depths.

FIG. 4 is a schematic diagram showing an example of steering angles set according to the image depths. As shown in FIG. 4, a larger steering angle may be set when the image depth is smaller. Also, a smaller steering angle may be set when the image depth is larger. That is, steering angles $\theta_1$ to $\theta_3$ of scan-lines $S_1$ to $S_n$ may be set in consideration of image depths $d_1$ to $d_3$ for a target object 210, as shown in FIG. 4.

Figure 5:
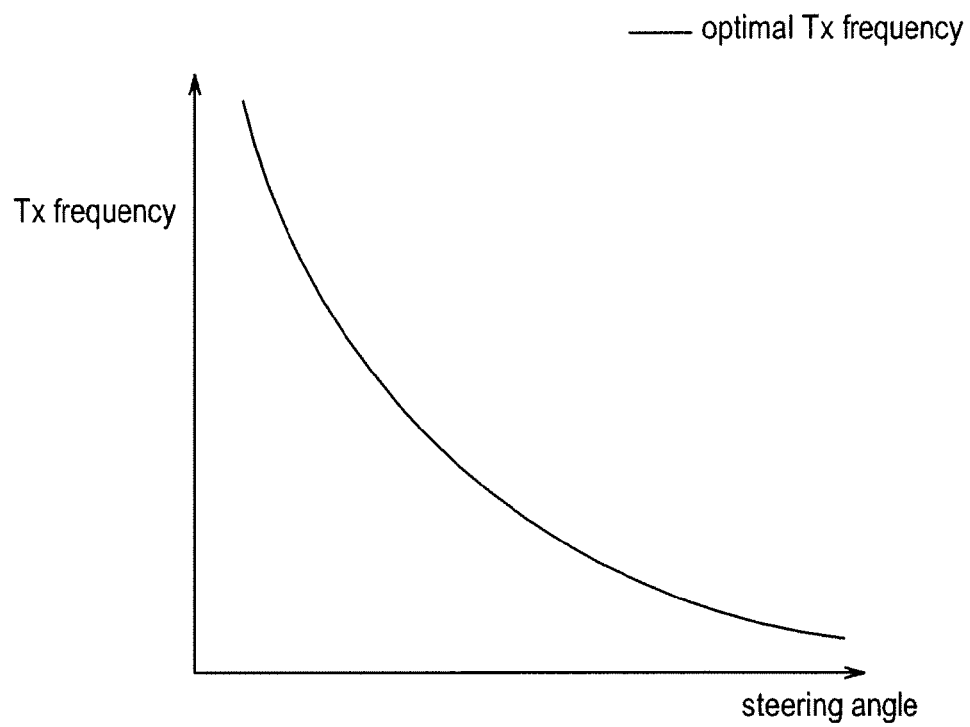
FIG. 5 is a graph showing an example of optimal Tx frequencies set according to steering angles.

FIG. 5 is a graph showing an example of optimal Tx frequencies set according to the steering angles. As shown in FIG. 5, a lower Tx frequency may be set as the optimal Tx frequency to decrease the grating lobe when a steering angle is larger. Also, a higher Tx frequency may be set as the optimal Tx frequency to decrease the grating lobe when the steering angle is smaller, as shown in FIG. 5.

Figure 6:
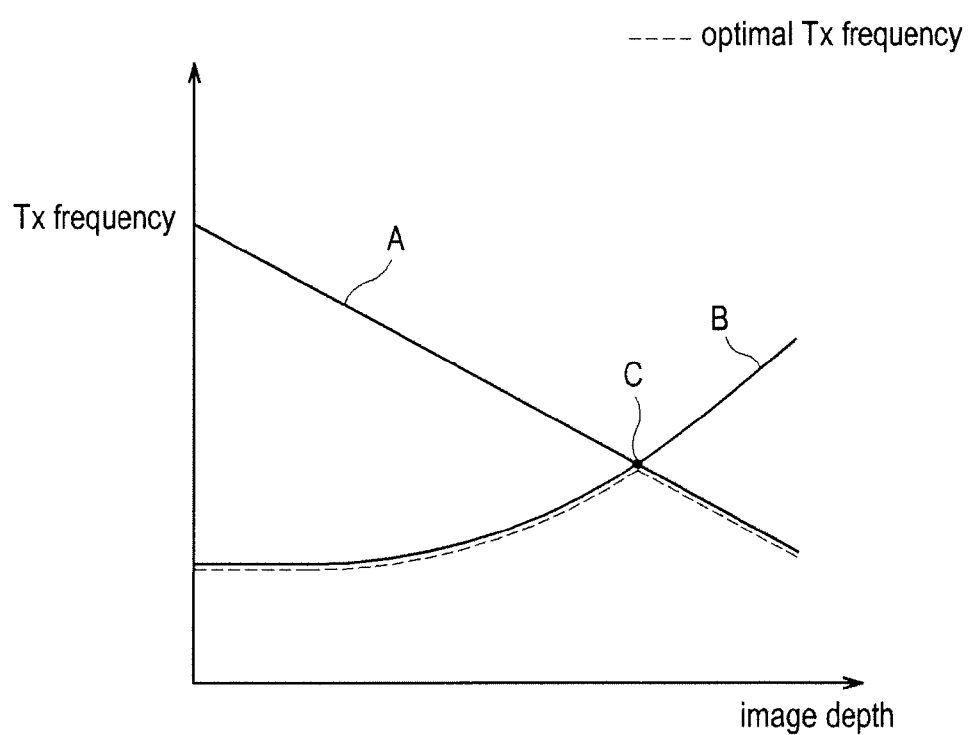
FIG. 6 is a schematic diagram showing an example of the optimal Tx frequencies set according to the image depths and steering angles.

FIG. 6 is a schematic diagram showing an example of the optimal Tx frequencies according to scan conditions (i.e., image depths and steering angles). When only an image depth for a target object is considered to set an optimal Tx frequency as in a conventional method, the resultant values may be obtained as indicated in A shown in FIG. 6. Also, when only a steering angle according to the image depth is considered to set an optimal Tx frequency as in the conventional method, the resultant values may be obtained as indicated in B, which is shown in FIG. 6. However, in this embodiment, both the image depth and the steering angle are considered to set an optimal Tx frequency.

When an image depth for the target object is less than a predetermined threshold value C (i.e., the target object is located on a near position from a surface of a subject, e.g., a patient), the optimal Tx frequency is set according to the steering angle as shown in FIG. 6 to decrease the grating lobe. Also, when the image depth for the target object is more than the predetermined threshold value C (i.e., the target object is located on a far position from the surface of the subject), the optimal Tx frequency is set according to the image depth as shown in FIG. 6 to decrease the grating lobe.

In one embodiment, the mapping table is a table for setting the Tx frequency in consideration of the steering angles when the image depth is less than the predetermined threshold value and setting the Tx frequency in consideration of the image depth when the image depth is more than the predetermined threshold value.

Referring back to FIG. 1, the ultrasound system 100 may further include an ultrasound data acquisition unit 130. The ultrasound data acquisition unit 130 may be configured to transmit and receive ultrasound signals to and from the target object to thereby output ultrasound data.

Figure 7:
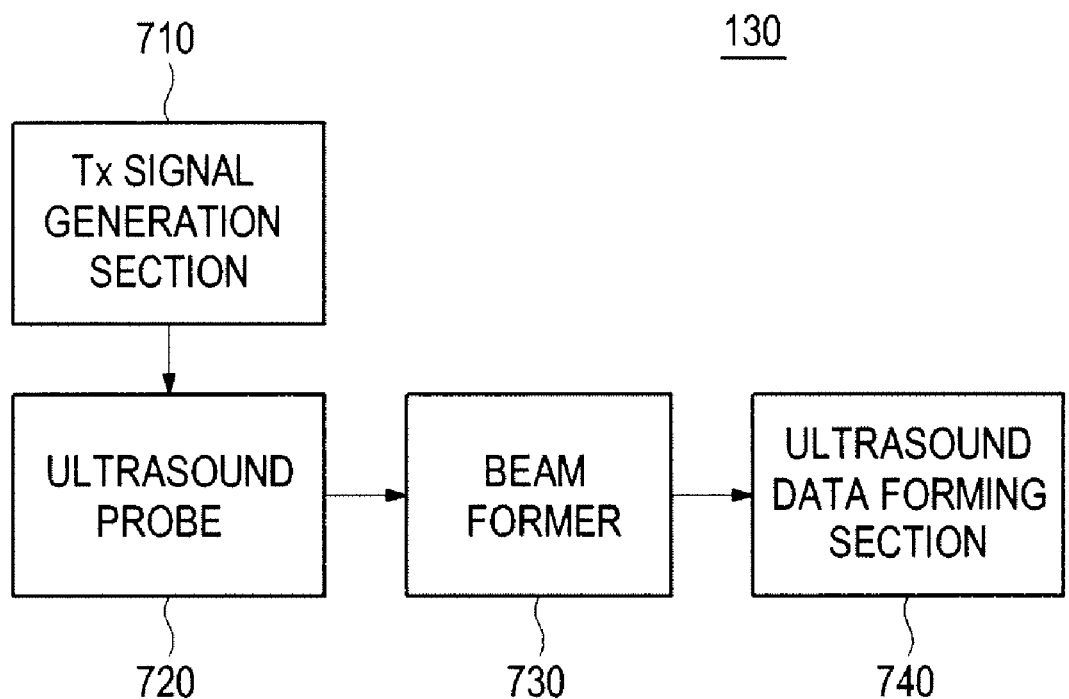
FIG. 7 is a block diagram showing an illustrative embodiment of an ultrasound data acquisition unit.

FIG. 7 is a block diagram showing an illustrative embodiment of the ultrasound data acquisition unit. Referring to FIG. 7, the ultrasound data acquisition unit 130 may include a transmit (Tx) signal generating section 710, an ultrasound probe 720, a beam former 730 and an ultrasound data forming section 740.

The Tx signal generating section 710 may be configured to generate Tx signals for obtaining the ultrasound image.

The ultrasound probe 720 may include a plurality of elements (not shown) for reciprocally converting between ultrasound signals and electrical signals. The ultrasound probe 720 may be configured to form ultrasound signals in response to the Tx signals provided from the Tx signal generating section 710 to thereby transmit the ultrasound signals into the target object. The ultrasound probe 720 may further receive ultrasound echo signals reflected from the target object to thereby form received signals. The received signals may be analog signals. The ultrasound probe 720 may include a linear probe, a convex probe, a 3D (three-dimensional) mechanical probe, a 2D (two-dimensional) array probe and the like. However, it should be noted herein that the ultrasound probe 720 may not be limited thereto.

The beam former 730 may be configured to convert the received signals provided from the ultrasound probe 720 into digital signals. The beam former 730 may further apply delays to the digital signals in consideration of distance between the elements and focal points to thereby output digital receive-focused signals.

The ultrasound data forming section 740 may be configured to form the ultrasound data based on the digital receive-focused signals provided from the beam former 730. The ultrasound data may be radio frequency (RF) data or in-phase/quadrature (IQ) data. However, it should be noted herein that the ultrasound data may not be limited thereto.

Referring back to FIG. 1, the ultrasound system 100 may further include a processing unit 140 in communication with the user input unit 110, the storage unit 120 and the ultrasound data acquisition unit 130. The processing unit 140 may be configured to form the ultrasound image based on the ultrasound data provided from the ultrasound data acquisition unit 130. The processing unit 140 may further analyze the ultrasound image to thereby set an optimal image parameter for obtaining an optimal ultrasound image. The image parameter may include a focal point position, a steering angle, a transmit (Tx) frequency and a sound speed. However, it should be noted herein that the image parameter may not be limited thereto.

The ultrasound system 100 may further comprise a display unit 150. The display unit 150 may display the ultrasound image formed by the processing unit 140. The display unit 150 may include a cathode ray tube (CRT), a liquid crystal display (LCD), an organic light emitting diodes (OLED) and the like. However, it should be noted herein that the display unit 150 may not be limited thereto.

Embodiments for setting the optimal image parameter may be described with reference to the accompanying drawings.

First Embodiment

Figure 8:
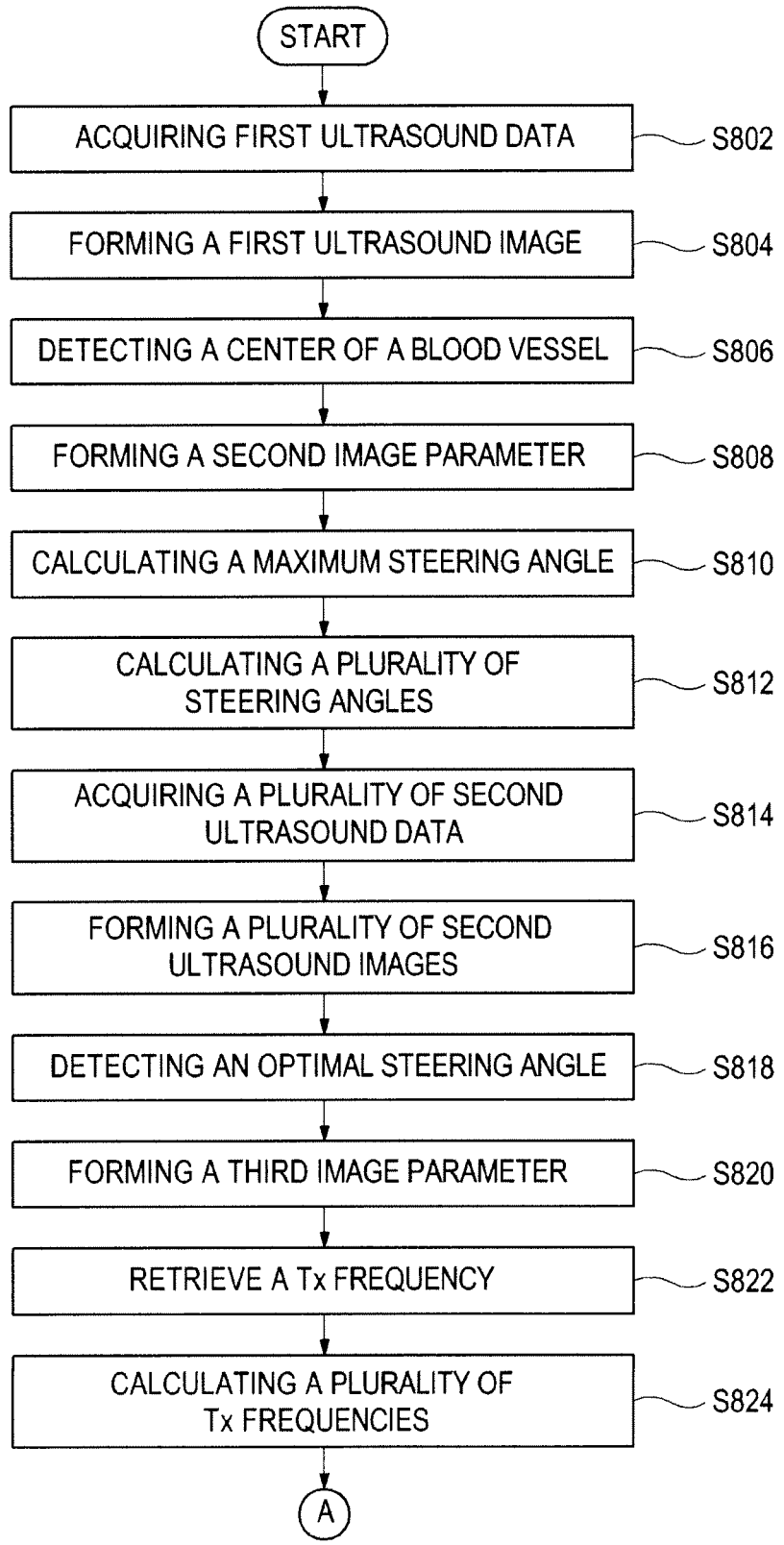
FIGS. 8 and 9 are a flow chart showing a process for setting an optimal image parameter according to a first embodiment of the present invention.
Figure 9:
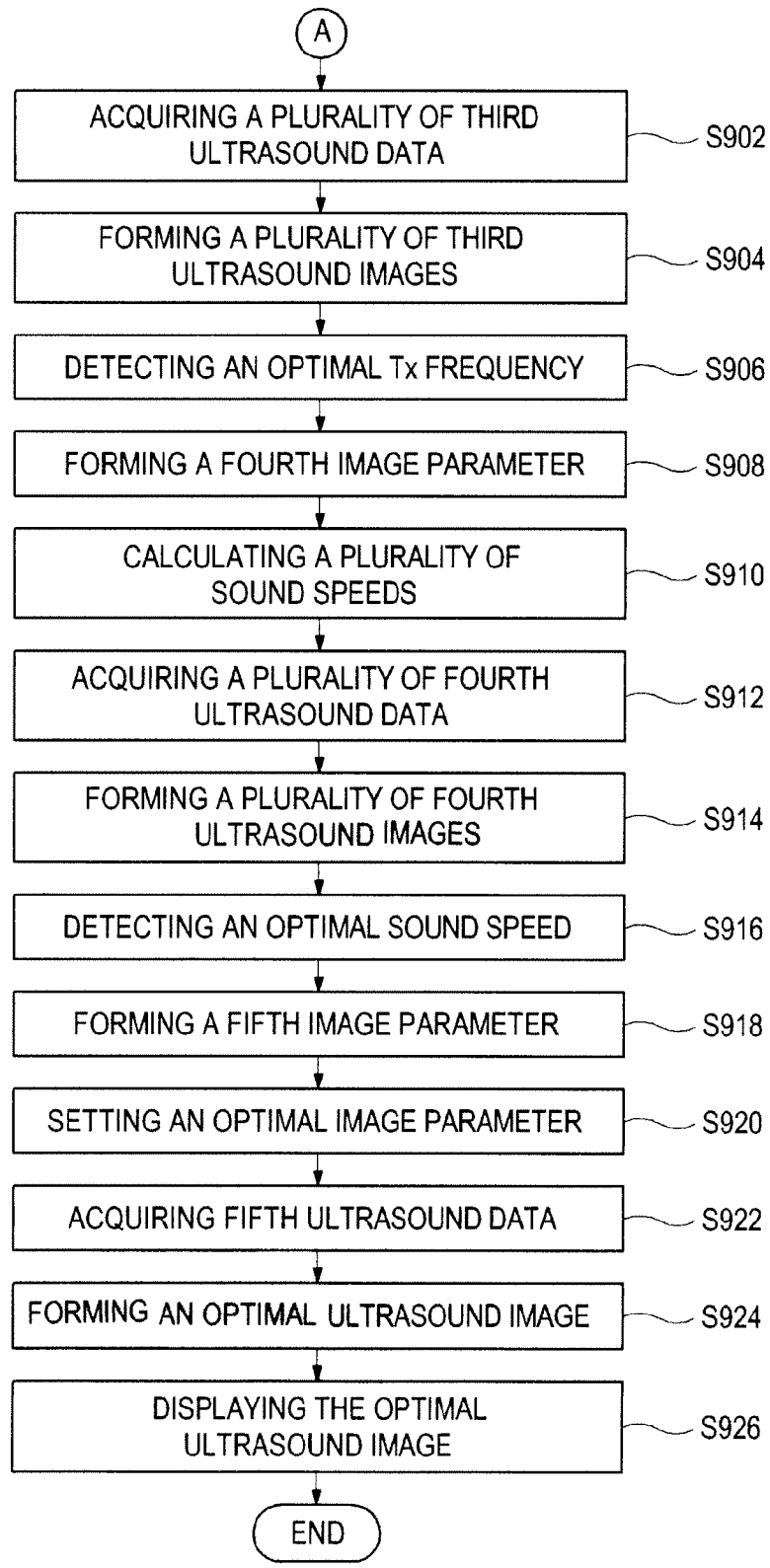

FIGS. 8 and 9 are flow charts showing a process of setting the optimal image parameter according to a first embodiment of the present invention. Referring to FIG. 8, the ultrasound data acquisition unit 130 may transmit and receive ultrasound signals to and from the target object in consideration of a predetermined image parameter (hereinafter, a first image parameter) to thereby output first ultrasound data at step S802.

More particularly, the Tx signal generating section 710 may generate first Tx signals for obtaining the ultrasound image in consideration of the first image parameter and the locations of the transducer elements. The ultrasound probe 720 may transmit ultrasound signals to the target object in response to the first Tx signals provided from the Tx signal generating section 710. The ultrasound probe 720 may further receive ultrasound echo signals reflected from the target object to thereby form first received signals. The beam former 730 may convert the first received signals provided from the ultrasound probe 720 into first digital signals. The beam former 730 may further apply delays to the first digital signals in consideration of the first image parameter and the locations of the transducer elements to thereby output first digital receive-focused signals. The ultrasound data forming section 740 may form the first ultrasound data based on the first digital receive-focused signals provided from the beam former 730.

The processing unit 140 may form a first ultrasound image based on the first ultrasound data provided from the ultrasound data acquisition unit 130 at step S804. The first ultrasound image may be displayed on the display unit 150.

The processing unit 140 may perform an image process upon the first ultrasound image to thereby detect a center of the blood vessel at step S806.

As one example, the processing unit 140 may retrieve the blood vessel template from the storage unit 120. The processing unit 140 may further locate the blood vessel template on the first ultrasound image. The processing unit 140 may further detect the blood vessel in the first ultrasound image while moving the blood vessel template by predetermined intervals. The blood vessel may be detected by using image processing methods such as a pattern matting method, a sum of absolute difference (SAD) method and the like. However, it should be noted herein that the image processing methods may not be limited thereto. The processing unit 140 may further detect a maximum diameter of the detected blood vessel. The processing unit 140 may further detect a center of the maximum diameter to thereby set the center of the maximum diameter as the center of the blood vessel.

Figure 10:
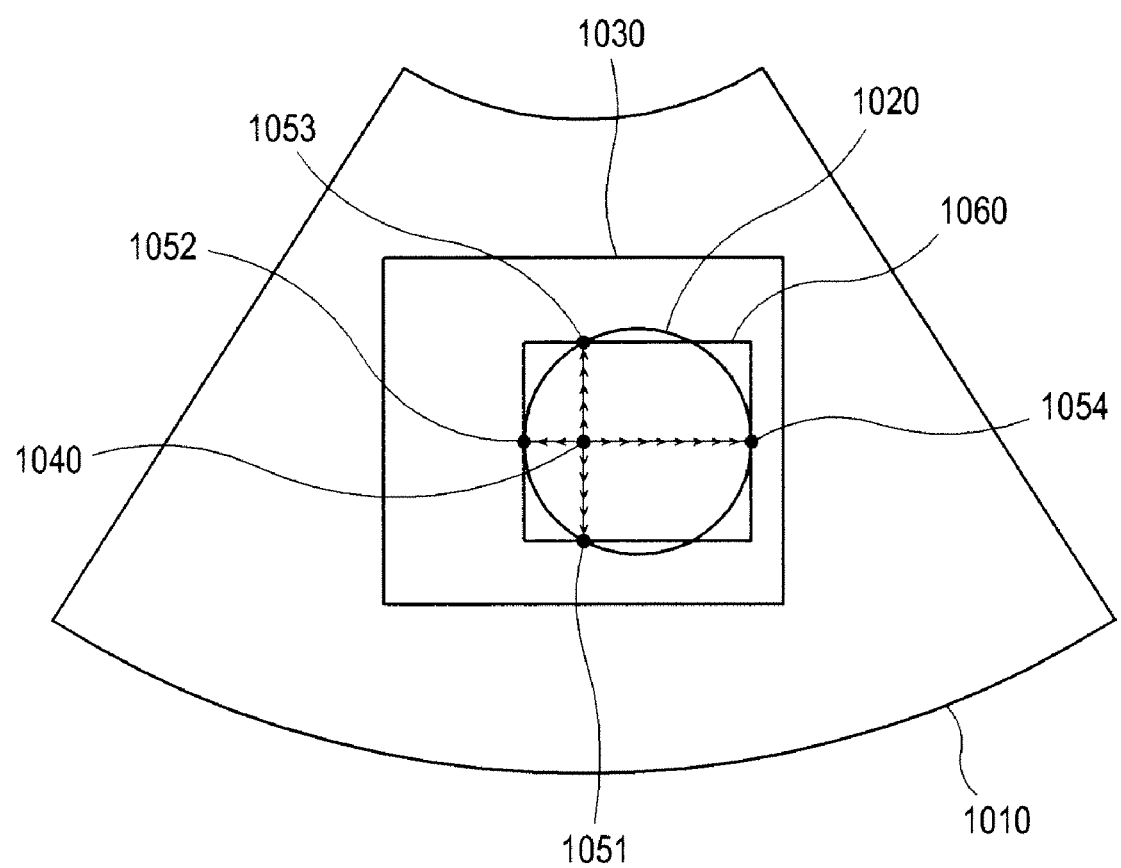
FIG. 10 is a schematic diagram showing an example of an ultrasound image, a region of interest (ROI) and a virtual rectangle.

FIG. 10 is a schematic diagram showing an example of the first ultrasound image, the ROI and a virtual rectangle. As another example, the processing unit 140 may set the ROI 1030 on the first ultrasound image 1010 based on the input information (i.e., first input information) provided from the user input unit 110, as shown in FIG. 10. The processing unit 140 may further detect a center 1040 of the ROI 1030. The processing unit 140 may further detect edge points 1051, 1052, 1053 and 1054 corresponding to the blood vessel wall 1020 while moving the center 1040 to each of up, down, right and left directions by predetermined intervals within the ROI 1030. The edge points 1051, 1052, 1053 and 1054 may have a maximum brightness difference between adjacent pixels in the first ultrasound image. Also, methods of detecting the edge points are well known in the art. Thus, they have not been described in detail so as not to unnecessarily obscure the present invention. The processing unit 140 may further set the virtual rectangle 1060 passing through the edge points 1051, 1052, 1053 and 1054. The processing unit 140 may further detect a center of the virtual rectangle 1060 to thereby set the center of the virtual rectangle 1060 as the center of the blood vessel.

Figure 11:
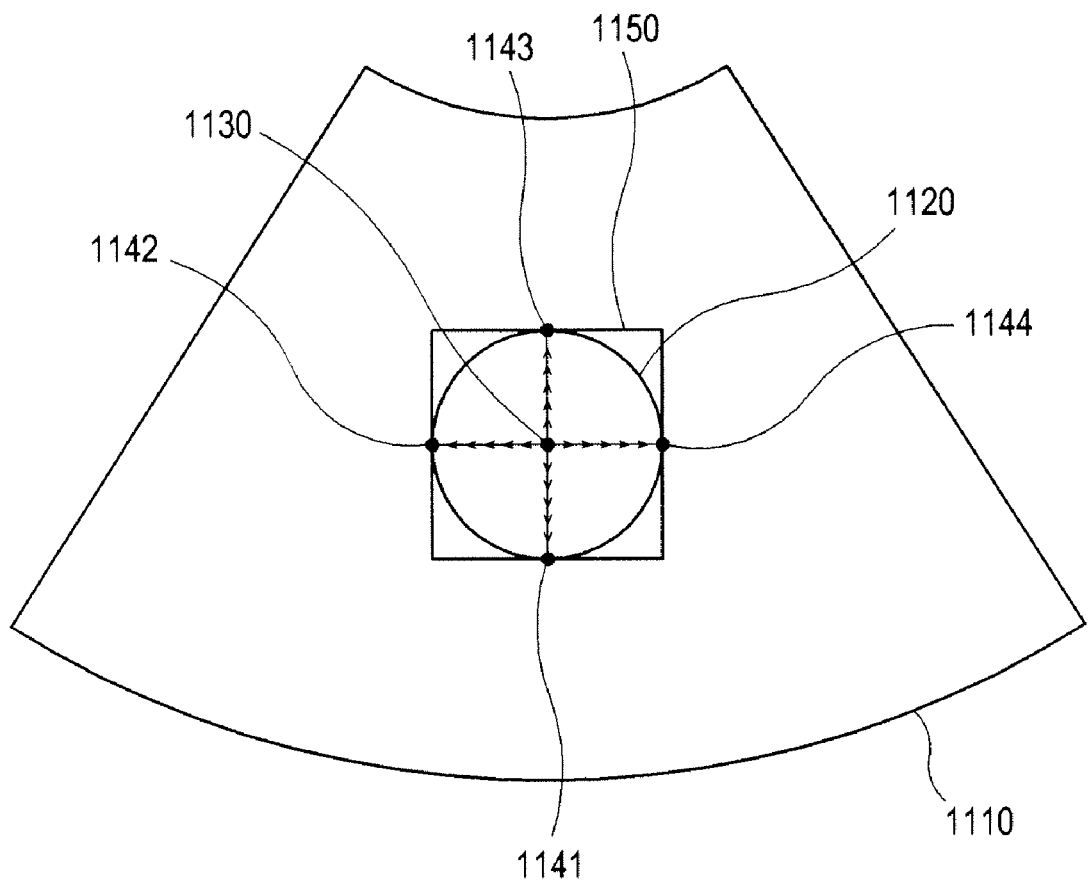
FIG. 11 is a schematic diagram showing an example of the ultrasound image, a seed point and the virtual rectangle.

FIG. 11 is a schematic diagram showing an example of the first ultrasound image, a seed point and the virtual rectangle. As yet another example, the processing unit 140 may set the seed point 1130 on the first ultrasound image 1110 based on the input information (i.e., second input information) provided from the user input unit 110, as shown in FIG. 11. The processing unit 140 may further detect edge points 1141, 1142, 1143 and 1144 corresponding to the blood vessel wall 1120 while moving the seed point 1130 to each of up, down, right and left directions by predetermined intervals. The edge points 1141, 1142, 1143 and 1144 may have a maximum brightness difference between adjacent pixels in the first ultrasound image. The processing unit 140 may further set the virtual rectangle 1150 passing through the edge points 1141, 1142, 1143 and 1144. The processing unit 140 may detect a center of the virtual rectangle 1150 to thereby set the center of the virtual rectangle 1150 as the center of the blood vessel.

Referring back to FIG. 8, the processing unit 140 may form a second image parameter with the focal point position as the center of the blood vessel at step S808. The steering angle, Tx frequency and sound speed of the second image parameter correspond to the steering angle, Tx frequency and sound speed of the first image parameter, respectively. The second image parameter may be stored in the storage unit 120.

Figure 12:
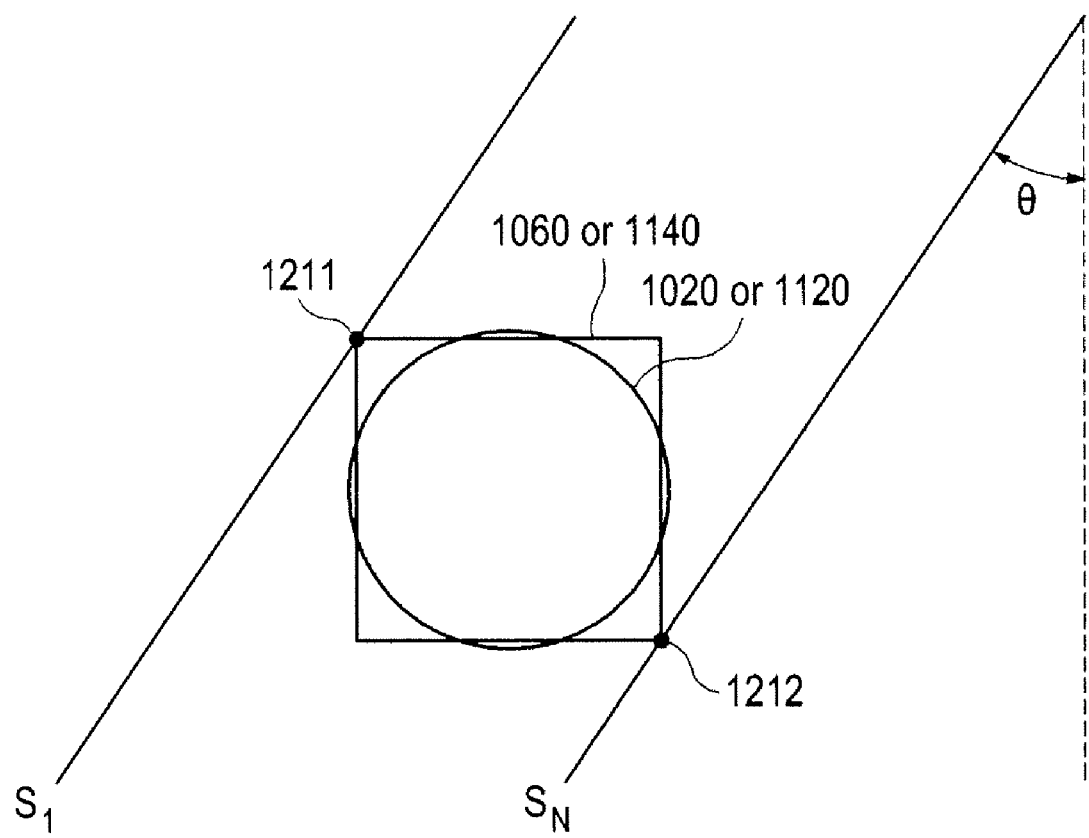
FIG. 12 is a schematic diagram showing an example of a maximum steering angle.

The processing unit 140 may calculate a maximum steering angle of scan-lines at step S810. As one example, the processing unit 140 may calculate a steering angle θ of a first scan-line $S_1$ passing through a vertex 1211 of the virtual rectangle 1060 or 1140 within the scan-lines $S_1$ to $S_N$, as shown in FIG. 12. The processing unit 140 may further set the steering angle θ as the maximum steering angle. As another example, the processing unit 140 may calculate a steering angle θ of a last scan-line $S_N$ passing through a vertex 1212 of the virtual rectangle 1060 or 1140 within the scan-lines $S_1$ to $S_N$, as shown in FIG. 12.

The processing unit 140 may calculate a plurality of steering angles based on the maximum steering angle at step S812. The steering angles may be calculated by increasing and/or decreasing the maximum steering angle by predetermined angles.

The ultrasound data acquisition unit 130 may transmit and receive ultrasound signals to and from the target object in consideration of the second image parameter and the steering angles to thereby output a plurality of second ultrasound data at step S814.

More particularly, the Tx signal generating section 710 may generate a plurality of second Tx signals for obtaining a plurality of second ultrasound images corresponding to the steering angles in consideration of the second image parameter and the locations of the transducer elements. The ultrasound probe 720 may transmit ultrasound signals to the target object in response to each of the second Tx signals provided from the Tx signal generating section 710. The ultrasound probe 720 may further receive ultrasound signals reflected from the target object to thereby form a plurality of second received signals. The beam former 730 may convert the second received signals provided from the ultrasound probe 720 into a plurality of second digital signals. The beam former 730 may further apply delays to the second digital signals in consideration of the second image parameter, the steering angles and the locations of the transducer elements to thereby output a plurality of second digital receive-focused signals. The ultrasound data forming section 740 may form the second ultrasound data based on the second digital receive-focused signals.

The processing unit 140 may form the second ultrasound images based on the second ultrasound data provided from the ultrasound data acquisition unit 130 at step 5816. The second ultrasound images may be displayed on the display unit 150.

The processing unit 140 may analyze the second ultrasound images to thereby detect an optimal steering angle from the plurality of steering angles at step S818.

As one example, the processing unit 140 may set a window having a predetermined size based on the detected blood vessel on each of the second ultrasound images. The processing unit 140 may further detect a signal to noise ratio (SNR), a number of edge points of the blood vessel and a contrast difference between pixels for the window. The processing unit 140 may further rate each of the detected SNR, the number of edge points and the contrast difference for each of the second ultrasound images. For example, if the SNR is −10 dB to −15 dB, then the SNR may be rated to 10. If the SNR is −16 dB to −30 dB, then the SNR may be rated to 5. Also, if the SNR is −31 dB to −40 dB, then the SNR may be rated to 0. In addition, if the number of edge points is less than 10, then the number of edge points may be graded to 0, If the number of edge points is 10 to 20, then the number of edge points may be rated to 5. Moreover, if the number of edge points is more than 21, then the number of edge points may be rated to 10. Further, if the contrast difference is less than 30, then the contrast difference may be rated to 0. If the contrast difference is 31 to 60, then the contrast difference may be rated to 5. If the contrast difference is more than 60, then the contrast difference may be rated to 10. The processing unit 140 may further compare the rated points of each of the second ultrasound images to thereby detect a second ultrasound image having a maximum point. The processing unit 140 may set the steering angle corresponding to the detected second ultrasound image as the optimal steering angle.

The processing unit 140 may form a third image parameter with the steering angle as the optimal steering angle at step 820. The focal point position, Tx frequency and sound speed of the third image parameter correspond to the focal point position, Tx frequency and sound speed of the second image parameter, respectively. The third image parameter may be stored in the storage unit 120.

The processing unit 140 may retrieve a Tx frequency corresponding to the center of the blood vessel and the optimal steering angle from the storage unit 120, as shown in FIG. 6, at step S822.

The processing unit 140 may calculate a plurality of Tx frequencies based on the retrieved Tx frequency at step S824. The Tx frequencies may be calculated by increasing and/or decreasing the retrieved Tx frequency by predetermined frequencies.

Referring to FIG. 9, the ultrasound data acquisition unit 130 may transmit and receive ultrasound signals to and from the target object in consideration of the third image parameter and the Tx frequencies to thereby output a plurality of third ultrasound data at step S902.

More particularly, the Tx signal generating section 710 may generate a plurality of third Tx signals for obtaining a plurality of third ultrasound images corresponding to the Tx frequencies in consideration of the third image parameter and the locations of the transducer elements. The ultrasound probe 720 may transmit ultrasound signals to the target object in response to each of the third Tx signals provided from the Tx signal generating section 710. The ultrasound probe 720 may further receive ultrasound echo signals reflected from the target object to thereby form a plurality of third received signals. The beam former 730 may convert the third received signals provided from the ultrasound probe 720 into a plurality of third digital signals. The beam former 730 may further apply delays to the third digital signals in consideration of the third image parameter and the locations of the transducer elements to thereby output a plurality of third digital receive-focused signals. The ultrasound data forming section 740 may form the third ultrasound data based on the third digital receive-focused signals.

The processing unit 140 may form the third ultrasound images based on the third ultrasound data provided from the ultrasound data acquisition unit 130 at step S904.

The processing unit 140 may analyze the third ultrasound images to thereby detect an optimal Tx frequency from the Tx frequencies at step S906. The method of detecting the optimal Tx frequency is similar to the method of detecting the optimal steering angle at step S818 in FIG. 8. Thus, it has not been described in detail.

The processing unit 140 may form a fourth image parameter with the Tx frequency as the optimal Tx frequency at step S908. The focal point position, steering angle and sound speed of the fourth image parameter correspond to the focal point position, steering angle and sound speed of the third image parameter, respectively. The fourth image parameter may be stored in the storage unit 120.

The processing unit 140 may calculate a plurality of sound speeds based on a reference sound speed (e.g., 1564 m/s) at step S910. The sound speeds may be calculated by increasing and/or decreasing the reference sound speed by predetermined intervals.

The ultrasound data acquisition unit 130 may transmit and receive ultrasound signals to and from the target object in consideration of the fourth image parameter and the sound speeds to thereby output a plurality of fourth ultrasound data at step S912.

More particularly, the Tx signal generating section 710 may generate a plurality of fourth Tx signals for obtaining a plurality of fourth ultrasound images corresponding to the sound speeds in consideration of the fourth image parameter and the locations of the transducer elements. The ultrasound probe 720 may transmit ultrasound signals to the target object in response to each of the fourth Tx signals provided from the Tx signal generating section 710. The ultrasound probe 720 may further receive ultrasound echo signals reflected from the target object to thereby form a plurality of fourth received signals. The beam former 730 may convert the fourth received signals provided from the ultrasound probe 720 into a plurality of fourth digital signals. The beam former 730 may further apply delays to the fourth digital signals in consideration of the fourth image parameter and the locations of the transducer elements to thereby output a plurality of fourth digital receive-focused signals. The ultrasound data forming section 740 may form the fourth ultrasound data based on the fourth digital receive-focused signals.

The processing unit 140 may form a plurality of fourth ultrasound image based on the fourth ultrasound data provided from the ultrasound data acquisition unit 130 at step S914.

The processing unit 140 may analyze the fourth ultrasound images to thereby detect an optimal sound speed from the sound speeds at step S916. The method of detecting the optimal sound speed is similar to the method of detecting the optimal steering angle at step S818 in FIG. 8. Thus, it has not been described in detail.

The processing unit 140 may form a fifth image parameter with the sound speed as the optimal sound speed at step S918. The focal point position, steering angle and Tx frequency of the fifth image parameter correspond to the focal point position, steering angle and Tx frequency of the fourth image parameter, respectively. The processing unit 140 may set the fifth image parameter as the optimal image parameter at step S920. The optimal image parameter may be stored in the storage unit 120.

The ultrasound data acquisition unit 130 may transmit and receive ultrasound signals to and from the target object in consideration of the optimal image parameter to thereby form fifth ultrasound data at step S922.

More particularly, the Tx signal generating section 710 may generate fifth Tx signals for obtaining an optimal ultrasound image in consideration of the optimal image parameter and the locations of the transducer elements. The ultrasound probe 720 may transmit ultrasound signals to the target object in response to the fifth Tx signals provided from the Tx signal generating section 710. The ultrasound probe 720 may further receive ultrasound echo signals reflected from the target object to thereby form fifth received signals. The beam former 730 may convert the fifth received signals provided from the ultrasound probe 720 into fifth digital signals. The beam former 730 may further apply delays to the fifth digital signals in consideration of the optimal image parameter and the locations of the transducer elements to thereby output fifth digital receive-focused signals. The ultrasound data forming section 740 may form the fifth ultrasound data based on the fifth digital receive-focused signals.

The processing unit 140 may form the optimal ultrasound image based on the fifth ultrasound data provided from the ultrasound data acquisition unit 130 at step S924.

The display unit 150 may display the optimal ultrasound image formed by the processing unit 140 at step S926.

While the image parameter may be optimized in order of the focal point position, the steering angle, the Tx frequency and the sound speed, the image parameter may be further optimized in various order of the focal point position, the steering angle, the Tx frequency and the sound speed as occasion demands.

Second Embodiment

Figure 13:
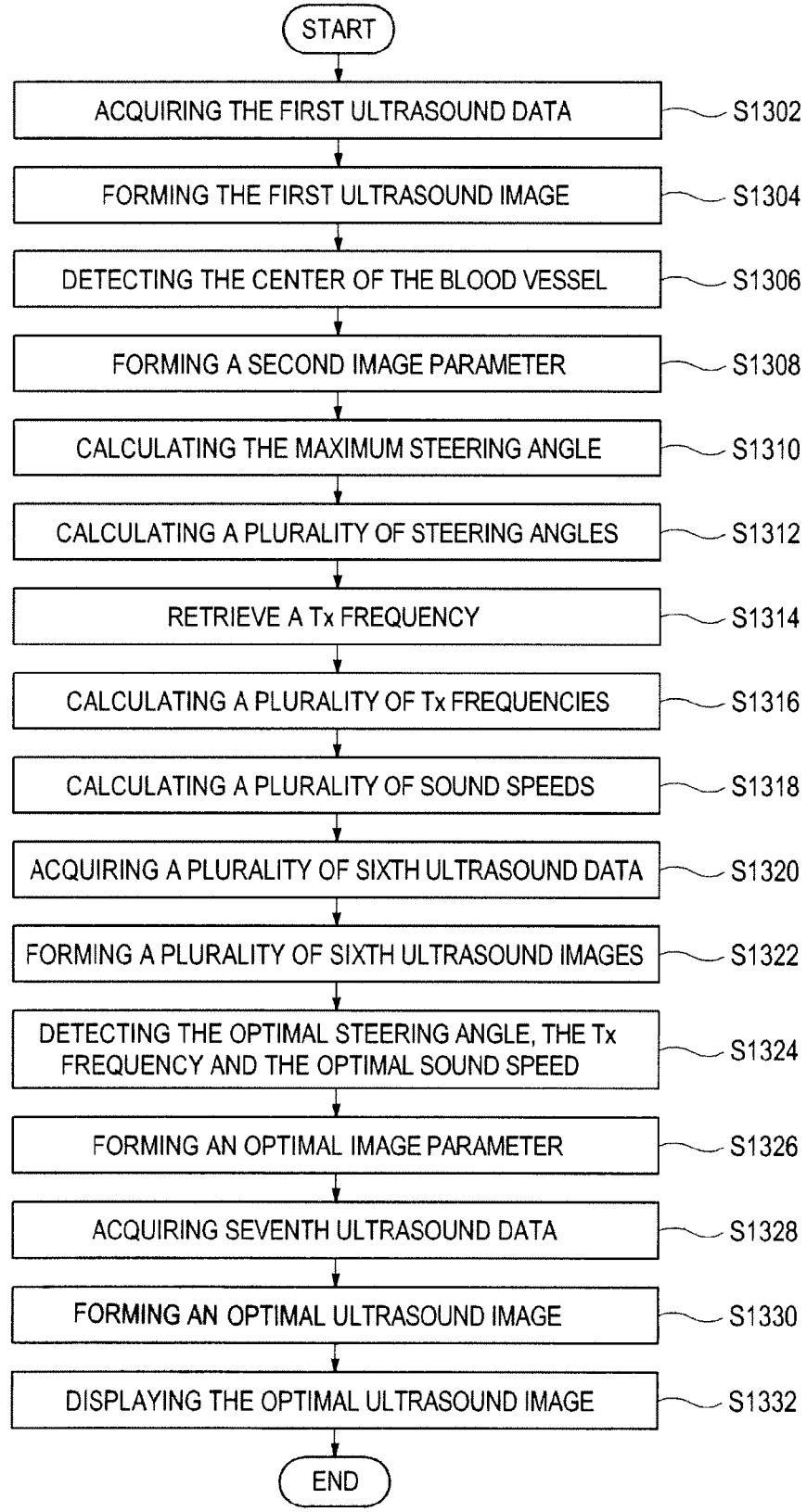
FIG. 13 is a flow chart showing a process for setting an optimal image parameter according to a second embodiment of the present invention.

FIG. 13 is a flow chart showing a process of setting an optimal image parameter according to a second embodiment of the present invention. Referring to FIG. 13, the ultrasound data acquisition unit 130 may transmit and receive ultrasound signals to and from the target object in consideration of the first image parameter to thereby output the first ultrasound data at step S1302. The step S1302 in the second embodiment is similar to the step S802 in the first embodiment. Thus, it has not been described in detail.

The processing unit 140 may form the first ultrasound image based on the first ultrasound data provided form the ultrasound data acquisition unit 130 at step S1304. The first ultrasound image may be displayed on the display unit 150.

The processing unit 140 may analyze the first ultrasound image to thereby detect the center of the blood vessel at step S1306. The step S1306 in the second embodiment is similar to the step S806 in the first embodiment. Thus, it has not been described in detail.

The processing unit 140 may form the second parameter with the focal point position as the center of the blood vessel at step S1308. The steering angle, Tx frequency and sound speed of the second image parameter correspond to the steering angle, Tx frequency and sound speed of the first image parameter, respectively. The second image parameter may be stored in the storage unit 120.

The processing unit 140 may calculate the maximum steering angle of the scan-lines at step S1310. The step S1310 in the second embodiment is similar to the step S810. Thus, it has not been described in detail.

The processing unit 140 may calculate the steering angles based on the maximum steering angle at step S1312. The steering angles may be calculated by increasing and/or decreasing the maximum steering angle by predetermined angles.

The processing unit 140 may retrieve a Tx frequency corresponding to the center of the blood vessel and the maximum steering angle from storage unit 120, as shown in FIG. 6, at step S1314. The processing unit 140 may calculate a plurality of Tx frequencies based on the retrieved Tx frequencies at the step S1316.

The processing unit 140 may calculate a plurality of sound speeds based on a reference sound speed (e.g., 1564 m/s) at step S1318. The sound speeds may be calculated by increasing and/or decreasing the reference sound speed by predetermined values.

The ultrasound data acquisition unit 130 may transmit and receive ultrasound signals to and from the target object in consideration of the second image parameter, the steering angles, the Tx frequencies and the sound speeds to thereby output a plurality of sixth ultrasound data at step S1320.

More particularly, the Tx signal generating section 710 may generate a plurality of sixth Tx signals corresponding to the steering angles, the Tx frequencies and the sound speeds in consideration of the second image parameter and the locations of the transducer elements. The ultrasound probe 720 may transmit ultrasound signals to the target object in response to each of the sixth Tx signals provided from the Tx signal generating section 710. The ultrasound probe 720 may further receive ultrasound echo signals reflected from the target object to thereby form a plurality of sixth received signals. The beam former 730 may convert the sixth received signals provided from the ultrasound probe 720 into a plurality of sixth digital signals. The beam former 730 may further apply delays to the sixth digital signals in consideration of the second image parameter and the locations of the transducer elements to thereby output a plurality of sixth digital receive-focused signals. The ultrasound data forming section 740 may form the sixth ultrasound data based on the sixth digital receive-focused signals.

The processing unit 140 may form a plurality of sixth ultrasound images based on the sixth ultrasound data provided from the ultrasound data acquisition unit 130 at step S1322.

The processing unit 140 may analyze the sixth ultrasound images to thereby detect the optimal steering angle, the optimal Tx frequency and the optimal sound speed at step S1324.

In one embodiment, the processing unit 140 may set a window having a predetermined size based on the detected blood vessel on each of the sixth ultrasound images. The processing unit 140 may further detect a signal to noise ratio (SNR), a number of edge points of the blood vessel and a contrast difference between pixels for the window. The processing unit 140 may further rate each of the detected SNR, the number of edge points and contrast difference for each of the sixth ultrasound images. For example, if the SNR is −10 dB to −15 dB, then the SNR may be rated to 10. If the SNR is −16 dB to −30 dB, then the SNR may be rated to 5. If the SNR is −31 dB to −40 dB, then the SNR may be rated to 0. In addition, if the number of edge points is less than 10, then the number of edge points may be graded to 0. If the number of edge points is 10 to 20, then the number of edge points may be rated to 5. If the number of edge points is more than 21, then the number of edge points may be rated to 10. Further, if the contrast difference is less than 30, then the contrast difference may be rated to 0. If the contrast difference is 31 to 60, then the contrast difference may be rated to 5. If the contrast difference is more than 60, then the contrast difference may be rated to 10. The processing unit 140 may further compare the rated points of each of the sixth ultrasound images to thereby detect a sixth ultrasound image having a maximum point. The processing unit 140 may set the steering angle, the Tx frequency and the sound speed corresponding to the detected sixth ultrasound image as the optimal steering angle, the optimal Tx frequency and the optimal sound speed, respectively.

The processing unit 140 may form an optimal image parameter based on the optimal steering angle, the optimal Tx frequency and the optimal sound speed at step S1326. The focal point position of the optimal image parameter corresponds to the focal point position of the second image parameter.

The ultrasound data acquisition unit 130 may transmit and receive ultrasound signals to and from the target object in consideration of the optimal image parameter to thereby form seventh ultrasound data at step S1328.

More particularly, the Tx signal generating section 710 may generate seventh Tx signals for obtaining an optimal ultrasound image in consideration of the optimal image parameter and the locations of the transducer elements. The ultrasound probe 720 may transmit ultrasound signals to the target object in response to the seventh Tx signals provided from the Tx signal generating section 710. The ultrasound probe 720 may further receive ultrasound echo signals reflected from the target object to thereby form seventh received signals. The beam former 730 may convert the seventh received signals provided from the ultrasound probe 720 into seventh digital signals. The beam former 730 may further apply delays to the seventh digital signals in consideration of the optimal image parameter and the locations of the transducer elements to thereby output seventh digital receive-focused signals. The ultrasound data forming section 740 may form the seventh ultrasound data based on the seventh digital receive-focused signals.

The processing unit 140 may form the optimal ultrasound image based on the seventh ultrasound data provided from the ultrasound data acquisition unit 130 at step S1330.

The display unit 150 may display the optimal ultrasound image formed by the processing unit 140 at step S1332.

Although embodiments have been described with reference to a number of illustrative embodiments thereof, it should be understood that numerous other modifications and embodiments can be devised by those skilled in the art that will fall within the spirit and scope of the principles of this disclosure. More particularly, numerous variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An ultrasound system, comprising:
an ultrasound data acquisition unit configured to transmit and receive ultrasound signals to and from a target object including a blood vessel to thereby output ultrasound data; and
a processing unit in communication with the ultrasound data acquisition unit and being configured to form an ultrasound image based on the ultrasound data, perform an image process upon the ultrasound image to thereby detect a center of the blood vessel from the ultrasound image, set the center of the blood vessel as an optimal focal point position, and calculate a plurality of steering angles, a plurality of transmit (Tx) frequencies and a plurality of sound speeds,
wherein the ultrasound data acquisition unit is further configured to transmit and receive ultrasound signals to and from the target object in consideration of each of the steering angles, the Tx frequencies and the sound speeds to thereby output a plurality of ultrasound data,
wherein the processing unit is further configured to form a plurality of ultrasound images corresponding to each of the steering angles, the Tx frequencies and the sound speeds based on the plurality of ultrasound data, detect a signal to noise ratio (SNR), a number of edge points of the blood vessel and a contrast difference between pixels for each of the plurality of ultrasound images to thereby set an optimal steering angle, an optimal Tx frequency and an optimal sound speed based on the SNR, the number of edge points and the contrast difference.

2. The ultrasound system of claim 1, further comprising:
a storage unit for storing a blood vessel template for detecting the blood vessel from the ultrasound image.

3. The ultrasound system of claim 2, wherein the processing unit is configured to:
retrieve the blood vessel template from the storage unit;
locate the blood vessel template on the ultrasound image;
detect the blood vessel in the ultrasound image while moving the blood vessel template by predetermined intervals;
detect a maximum diameter of the detected blood vessel; and
detect a center of the maximum diameter to thereby set the center of the maximum diameter as the center of the blood vessel.

4. The ultrasound system of claim 1, further comprising:
a user input unit configured to receive input information for setting a region of interest (ROI) on the ultrasound image.

5. The ultrasound system of claim 4, wherein the processing unit is configured to:
set the ROI on the ultrasound image based on the input information;
detect a center of the ROI;
detect edge points corresponding to a blood vessel wall while moving the center of the ROI to each of up, down, right and left directions by predetermined intervals;
set a virtual rectangle passing through the edge points; and
detect a center of the virtual rectangle to thereby set the center of the virtual rectangle as the center of the blood vessel.

6. The ultrasound system of claim 5, wherein the processing unit is configured to:
detect a maximum steering angle of a scan-line passing through a vertex of the virtual rectangle;
increase/decrease the maximum steering angle by predetermined angles to thereby calculate the plurality of steering angles;
form the plurality of ultrasound images corresponding to the plurality of steering angles based on the plurality of ultrasound data;
set a window on each of the plurality of ultrasound images based on the blood vessel;
detect the SNR, the number of edge points and the contrast difference for the window;
rate each of the SNR, the number of edge points and the contrast difference for each of the plurality of ultrasound images;
compare the rated points of the plurality of ultrasound images to thereby detect an ultrasound image having a maximum point; and
set the steering angle corresponding to the detected ultrasound image as the optimal steering angle.

7. The ultrasound system of claim 1, further comprising:
a user input unit configured to receive input information for setting a seed point on the ultrasound image.

8. The ultrasound system of claim 7, wherein the processing unit is configured to:
set the seed point on the ultrasound image based on the input information;
detect edge points corresponding to a blood vessel wall while moving the seed point to each of up, down, right and left directions by predetermined intervals;
set a virtual rectangle passing through the edge points; and
detect a center of the virtual rectangle to thereby set the center of the virtual rectangle as the center of the blood vessel.

9. The ultrasound system of claim 1, further comprising:
a storage unit for storing a mapping table including Tx frequencies and steering angles.

10. The ultrasound system of claim 9, wherein the processing unit is configured to:
retrieve a Tx frequency corresponding to the optimal steering angle from the storage unit;
increase/decrease the retrieved Tx frequency by predetermined frequencies to thereby calculate the plurality of Tx frequencies;
form the plurality of ultrasound images corresponding to the plurality of Tx frequencies based on the plurality of ultrasound data;
set a window based on the blood vessel on each of the plurality of ultrasound images;
detect the SNR, the number of edge points and the contrast difference for the window;
rate each of the SNR, the number of edge points and the contrast difference for each of the plurality of ultrasound images;
compare the rated points of the plurality of ultrasound images to thereby detect an ultrasound image having a maximum point; and
set the Tx frequency corresponding to the detected ultrasound image as the optimal Tx frequency.

11. The ultrasound system of claim 1, wherein the processing unit is configured to:
increase/decrease a reference sound speed by predetermined values to thereby calculate the plurality of sound speeds;
form the plurality of ultrasound images corresponding to the plurality of sound speeds based on the plurality of ultrasound data;
set a window based on the blood vessel on each of the plurality of ultrasound images;
detect the SNR, the number of edge points and the contrast difference for the window;
rate each of the SNR, the number of edge points and the contrast difference for each of the plurality of ultrasound images;
compare the rated points of the plurality of ultrasound images to thereby detect an ultrasound image having a maximum point; and
set the sound speed corresponding to the detected ultrasound image as the optimal sound speed.

12. A method of setting an optimal image parameter, comprising:
a) forming a first ultrasound image based on ultrasound data for a target object including a blood vessel;
b) performing an image process upon the first ultrasound image to thereby detect a center of the blood vessel from the first ultrasound image;
c) setting the center of the blood vessel as an optimal focal point position;
d) forming a plurality of second ultrasound images corresponding to a plurality of steering angles for steering scan-lines, wherein the steering angles are calculated by increasing/decreasing a maximum steering angle by predetermined angles;
e) detecting a signal to noise ratio (SNR), a number of edge points of the blood vessel and a contrast difference between pixels for each of the second ultrasound images to thereby set an optimal steering angle based on the SNR, the number of edge points and the contrast difference;

f) forming a plurality of third ultrasound images corresponding to a plurality of transmit (Tx) frequencies, wherein the Tx frequencies are calculated by increasing/decreasing a Tx frequency corresponding to the optimal steering angle by predetermined frequencies;

g) detecting the SNR, the number of edge points and the contrast difference for each of the third ultrasound images to thereby set an optimal Tx frequency based on the SNR, the number of edge points and the contrast difference of the third ultrasound images;

h) forming a plurality of fourth ultrasound images corresponding to a plurality of sound speeds, wherein the sound speeds are calculated by increasing/decreasing a reference sound speed by predetermined values; and i) detecting the SNR, the number of edge points and the contrast difference for each of the fourth ultrasound images to thereby set an optimal sound speed based on the SNR, the number of edge points and the contrast difference of the fourth ultrasound images.

13. The method of claim 12, wherein the step b) comprises:
locating a blood vessel template corresponding to the blood vessel on the first ultrasound image;
detecting the blood vessel in the first ultrasound image while moving the blood vessel template by predetermined intervals;
detecting a maximum diameter of the detected blood vessel; and
detecting a center of the maximum diameter to thereby set the center of the maximum diameter as the center of the blood vessel.

14. The method of claim 12, wherein the step b) comprises:
setting a region of interest (ROI) on the first ultrasound image based on user input information;
detecting a center of the ROI;
detecting edge points corresponding to a blood vessel wall while moving the center of the ROI to each of up, down, right and left directions by predetermined intervals;
setting a virtual rectangle passing through the edge points; and
detecting a center of the virtual rectangle to thereby set the center of the virtual rectangle as the center of the blood vessel.

15. The method of claim 14, wherein the step d) comprises:
detecting the maximum steering angle of a scan-line passing through a vertex of the virtual rectangle;
increasing/decreasing the maximum steering angle by predetermined angles to thereby calculate the plurality of steering angles; and
forming a plurality of second ultrasound images based on the plurality of ultrasound data.

16. The method of claim 15, wherein the step e) comprises:
setting a window on each of the plurality of second ultrasound images based on the blood vessel;
detecting the SNR, the number of edge points and the contrast difference for the window;
rating each of the SNR, the number of edge points and the contrast difference for each of the plurality of second ultrasound images;
comparing the rated points of the plurality of second ultrasound images to thereby detect an ultrasound image having a maximum point; and
setting the steering angle corresponding to the detected ultrasound image as the optimal steering angle.

17. The method of claim 12, wherein the step b) comprises:
setting a seed point on the first ultrasound image based on user input information;
detecting edge points corresponding to a blood vessel wall while moving the seed point to each of up, down, right and left directions by predetermined intervals;
setting a virtual rectangle passing through the edge points; and
detecting a center of the virtual rectangle to thereby set the center of the virtual rectangle as the center of the blood vessel.

18. The method of claim 12, wherein the step f) comprises:
retrieving a Tx frequency corresponding to the optimal steering angle from a mapping table including Tx frequencies and steering angles;
increasing/decreasing the retrieved Tx frequency by predetermined frequencies to thereby calculate the plurality of Tx frequencies; and
forming a plurality of third ultrasound images based on the plurality of ultrasound data.

19. The method of claim 12, wherein the step g) comprises:
setting a window on each of the plurality of third ultrasound images based on the blood vessel;
detecting the SNR, the number of edge points and the contrast difference for the window;
rating each of the SNR, the number of edge points and the contrast difference for each of the plurality of third ultrasound images;
comparing the rated points of the plurality of third ultrasound images to thereby detect an ultrasound image having a maximum point; and
setting the Tx frequency corresponding to the detected ultrasound image as the optimal Tx frequency.

20. The method of claim 12, wherein the step i) comprises:
setting a window on each of the plurality of fourth ultrasound images based on the blood vessel;
detecting the SNR, the number of edge points and the contrast difference for the window;
rating each of the SNR, the number of edge points and the contrast difference for each of the plurality of fourth ultrasound images;
comparing the rated points of the plurality of fourth ultrasound images to thereby detect an ultrasound image having a maximum point; and
setting the sound speed corresponding to the detected ultrasound image as the optimal sound speed.

21. A method of setting an optimal image parameter, comprising:

a) acquiring ultrasound data of a target object including a blood vessel;

b) forming an ultrasound image based on the ultrasound data;

c) performing an image process upon the ultrasound image to thereby detect a center of the blood vessel from the ultrasound image;

d) setting the center of the blood vessel as an optimal focal point position;

e) calculating a plurality of steering angles, a plurality of transmit (Tx) frequencies and a plurality of sound speeds;

f) acquiring a plurality of ultrasound data of the target object in consideration of each of the steering angles, the Tx frequencies and the sound speeds;

g) forming a plurality of ultrasound images corresponding to each of the steering angles, the Tx frequencies and the sound speeds based on the plurality of ultrasound data;

h) detecting a signal to noise ratio (SNR), a number of edge points of the blood vessel and a contrast difference between pixels for each of the plurality of ultrasound images to thereby set an optimal steering angle, an optimal Tx frequency and an optimal sound speed based on the SNR, the number of edge points and the contrast difference.

22. The method of claim 21, wherein the step c) comprises:
locating a blood vessel template corresponding to the blood vessel on the ultrasound image;
detecting the blood vessel in the ultrasound image while moving the blood vessel template by predetermined intervals;
detecting a maximum diameter of the detected blood vessel; and
detecting a center of the maximum diameter to thereby set the center of the maximum diameter as the center of the blood vessel.

23. The method of claim 21, wherein the step c) comprises:
setting a region of interest (ROI) on the ultrasound image based on user input information;
detecting a center of the ROI;
detecting edge points corresponding to a blood vessel wall while moving the center of the ROI to each of up, down, right and left directions by predetermined intervals;
setting a virtual rectangle passing through the edge points; and
detecting a center of the virtual rectangle to thereby set the center of the virtual rectangle as the center of the blood vessel.

24. The method of claim 23, wherein the step e) comprises:
detecting a maximum steering angle of a scan-line passing through a vertex of the virtual rectangle;
increasing/decreasing the maximum steering angle by predetermined angles to thereby calculate the plurality of steering angles;
retrieving a Tx frequency corresponding to the maximum steering angle from a mapping table including Tx frequencies and steering angles;
increasing/decreasing the retrieved Tx frequency by predetermined frequencies to thereby calculate the plurality of Tx frequencies; and
increasing/decreasing a reference sound speed by predetermined values to thereby calculate the plurality of sound speeds.

25. The method of claim 21, wherein the step c) comprises:
setting a seed point on the first ultrasound image based on user input information;
detecting edge points corresponding to a blood vessel wall while moving the seed point to each of up, down, right and left directions by predetermined intervals;
setting a virtual rectangle passing through the edge points; and
detecting a center of the virtual rectangle to thereby set the center of the virtual rectangle as the center of the blood vessel.

26. The method of claim 21, wherein the step h) comprises:
setting a window on each of the plurality of ultrasound images based on the blood vessel;
detecting the SNR, the number of edge points and the contrast difference for the window;
rating each of the SNR, the number of edge points and the contrast difference for each of the plurality of ultrasound images;
comparing the rated points of the plurality of ultrasound images to thereby detect an ultrasound image having a maximum point; and
setting the steering angle, the Tx frequency and the sound speed corresponding to the detected ultrasound image as the optimal steering angle, the optimal Tx frequency and the optimal sound speed.

* * * * *